(12) United States Patent
Xu et al.

(10) Patent No.: US 8,933,234 B2
(45) Date of Patent: Jan. 13, 2015

(54) O-AMINO BENZONITRILE COMPOUNDS, METHOD FOR PREPARING SAME AND USES THEREOF

(71) Applicant: Hangzhou Udragon Chemical Co., Ltd., Hangzhou (CN)

(72) Inventors: Liangzhong Xu, Hangzhou (CN); Hualong Wu, Hangzhou (CN); Xianguo Feng, Hangzhou (CN); Shukun Gao, Hangzhou (CN); Ying Shi, Hangzhou (CN); Zongling Han, Hangzhou (CN); Xiaowei Liu, Hangzhou (CN); Haifeng Fu, Hangzhou (CN); Jingjing Liang, Hangzhou (CN)

(73) Assignee: Hangzhou Udragon Chemical Co., Ltd., Hangzhou, Zhejiang (CN)

( * ) Notice: Subject to any disclaimer, the term of this patent is extended or adjusted under 35 U.S.C. 154(b) by 0 days.

(21) Appl. No.: 14/347,644

(22) PCT Filed: Sep. 26, 2012

(86) PCT No.: PCT/CN2012/081965
§ 371 (c)(1),
(2) Date: Mar. 27, 2014

(87) PCT Pub. No.: WO2013/044791
PCT Pub. Date: Apr. 4, 2013

(65) Prior Publication Data
US 2014/0243376 A1    Aug. 28, 2014

(30) Foreign Application Priority Data

Sep. 29, 2011  (CN) .......................... 2011 1 0292240

(51) Int. Cl.
| | | |
|---|---|---|
| *C07D 401/00* | (2006.01) | |
| *A01N 43/40* | (2006.01) | |
| *A01N 43/56* | (2006.01) | |
| *C07D 401/04* | (2006.01) | |
| *C07D 401/14* | (2006.01) | |

(52) U.S. Cl.
CPC .............. *A01N 43/56* (2013.01); *C07D 401/04* (2013.01); *C07D 401/14* (2013.01)
USPC ........................................ 546/275.4; 514/341

(58) Field of Classification Search
USPC ........................................ 546/275.4; 514/341
See application file for complete search history.

*Primary Examiner* — Nizal Chandrakumar
(74) *Attorney, Agent, or Firm* — CBM Patent Consulting, LLC

(57) ABSTRACT

It relates to an anthranilonitrile compound, and to the process for preparing the said anthranilonitrile compound, and to its use. The anthranilonitrile compound has a chemical general formula (I). The compound of the general formula (I) has excellent pesticidal activity, can be used to control pests, and has more than 98% of mortality in 3 days to diamondback moth and pink borer.

9 Claims, No Drawings

O-AMINO BENZONITRILE COMPOUNDS, METHOD FOR PREPARING SAME AND USES THEREOF

This application is the U.S. national phase of International Application No. PCT/CN2012/081965 Filed 26 Sep. 2012 which designated the U.S. and claims priority to Chinese Application Nos. 201110292240.X filed 29 Sep. 2011, the entire contents of each of which are hereby incorporated by reference.

FIELD OF INVENTION

The present invention belongs to the field of insecticides. More specifically, the present invention relates to an anthranilonitrile compound, and to the process for preparing the said anthranilonitrile compound, and to its use.

BACKGROUND OF THE INVENTION

The pests, especially the agricultural insects have produced different degrees of resistance to the existing pesticides. It is an important means of pest resistance management to develop pesticides with new and different action mechanisms. With the improvement of people's need in the life quality and health, it has become an inevitable trend to research and develop the efficient, safe and green pesticides. DuPont disclosed an anthranilamide compound having insecticidal role in CN1678192A, whose chemical structure is as follows:

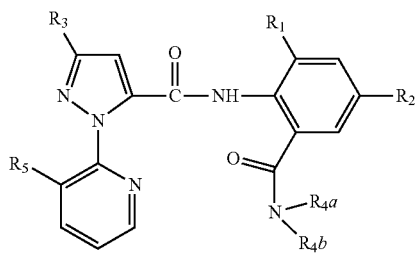

The derivatives involved in the patents or patent applications WO03015519, WO2004033468, CN101333213A and CN101298435A are all anthranilamide compounds. The anthranilonitrile compound, method for preparing and uses of which disclosed in the present invention have not been reported in the prior art. As found in the research by the inventor, using the anthranilonitrile compound of the present invention or the composition comprising the anthranilonitrile compound of the present invention in the prevention and control of pests in the field of the agriculture, forestry and animal husbandry, such as bollworm, diamondback moth, borer, can improve the actual control efficiency, expand the bactericidal spectrum and reduce the medication cost, which means it is an important means of integrated prevention and control of disease.

DETAILED DESCRIPTION OF THE INVENTION

[Technical Question to be Solved]
One object of the present invention is to provide an anthranilonitrile compound.
Another object of the present invention is to provide the process for preparing the said anthranilonitrile compound.
Another object of the present invention is to provide the use of the said anthranilonitrile compound.

[Technical Plan]
The present invention is achieved by the following technical plan.
The present invention relates to an anthranilonitrile compound, which has a chemical structural formula shown in the following general formula (I):

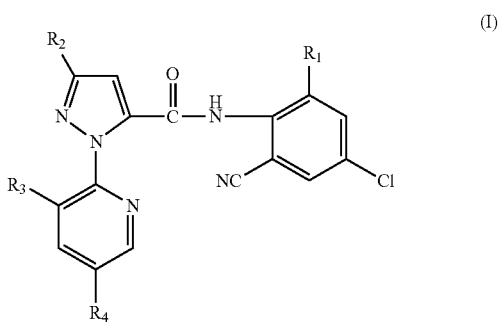

in which,
$R_1$ is selected from Cl, Br or methyl;
$R_2$ is selected from Br, Cl, $CF_3$, propynyloxy or haloalkoxy; the halogen in the said haloalkoxy is one or more halogen(s) selected from fluorine, chlorine or bromine;
$R_3$ is selected from Cl or F;
$R_4$ is selected from H, Cl or $CF_3$.
Preferably, in the general formula (I) of the said anthranilonitrile compound:
$R_1$ is selected from Cl, Br or methyl;
$R_2$ is selected from Cl, Br or $CF_3$;
$R_3$ is selected from Cl or F;
$R_4$ is selected from H or Cl.
More preferably, in the general formula (I) of the said anthranilonitrile compound:
$R_1$ is selected from Cl or methyl;
$R_2$ is selected from Cl or Br;
$R_3$ is selected from Cl or F;
$R_4$ is selected from H or Cl.
The present invention also relates to the process for preparing the anthranilonitrile compound of the general formula (I).
The steps of the process are as follows:
In a polar aprotic solvent and at temperature between −10 and 40° C., the following compound A is reacted with ammonia or liquid ammonia to give compound B; And then
In an aprotic solvent and at temperature between 20 and 120° C., the said compound B is reacted with dehydrating agent C to obtain the compound of the following general formula (I):

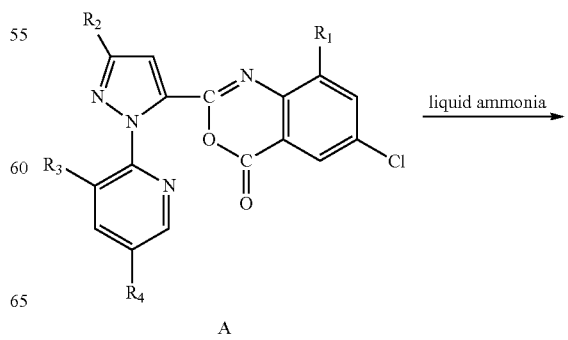

A

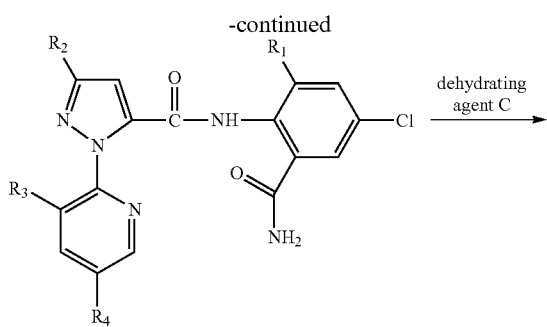

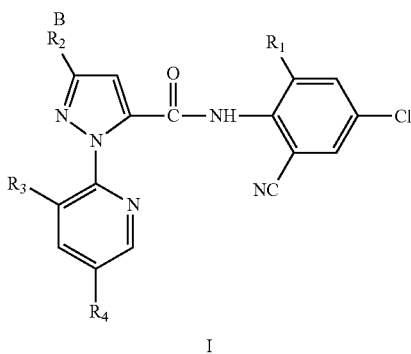

in which,

R₁, R₂, R₃ and R₄ are as defined above;

The said dehydrating agent C is $POCl_3$, $P_2O_5$, phosgene or solid phosgene.

The said polar aprotic solvent is amides or nitrile solvent.

The said amides solvent is N,N-dimethylformamide, N,N-dimethylacetamide or N-methylpyrrolidone.

Preferably, the said amides solvent is N,N-dimethylformamide.

The said nitrile solvent is acetonitrile or propionitrile.

Preferably, the said nitrile solvent is acetonitrile.

The said aprotic solvent is nitrile, esters or benzol solvent.

The said nitrile solvent is acetonitrile or propionitrile; the said esters solvent is ethyl acetate; the said benzol solvent is toluene.

According to one preferable embodiment of the present invention, the said compound A is reacted with ammonia or liquid ammonia at temperature between −5 and 10° C. to obtain the said compound B.

According to other preferable embodiment of the present invention, the compound B is reacted with dehydrating agent C at temperature between 70 and 90° C. to obtain the compound of the said general formula (I).

The chemical structure of the compound of general formula (I) of the present invention is characterized with nuclear magnetic resonance spectrometry.

In the method of the present invention, the said starting compound A can be prepared by using a conventionally known method, for example, obtained according to the method described in CN1541063A.

The present invention relates to an insecticidal composition. The said insecticidal composition comprises 0.1-80.0% of the compound of the said general formula (I) as active ingredient by weight and 20.0-99.9% of the pesticidally acceptable carriers and auxiliaries by weight.

Preferably, the insecticidal composition comprises 5.0-30.0% of the compound of general formula (I) as active ingredient by weight and 70.0-95.0% of the pesticidally acceptable carriers and auxiliaries by weight.

Unless otherwise specified, "%" involved in the present invention refers to "percentage by weight".

The formulation of the composition is suspension, oil suspension, water dispersible granules, aqueous emulsion, microemulsion or emulsifiable concentrate.

The suspension can be formulated by the skilled in the art by using the conventional preparation methods with dispersant, wetting agent, thickener, preservative, antifoaming agent and antifreezing agent.

The said dispersant is selected from the group consisting of polycarboxylates, lignin sulfonates, alkylnaphthalene sulfonates or TERSPERSE 2425 (produced by Huntsman Corporation, alkylnaphthalene sulfonates).

The said wetting agent is selected from the group consisting of alkylphenol polyoxyethylene ether formaldehyde condensate sulfates, alkylphenol polyoxyethylene ether phosphate, phenethyl phenol polyoxyethylene ether phosphates, alkyl sulfate, alkyl sulfonate, naphthalene sulfonate or TERSPERSE 2500 (produced by Huntsman Corporation).

The said thickener is selected from the group consisting of xanthan gum, magnesium aluminum silicate or bentonite.

The aid preservative is selected from the group consisting of benzoic acid, sodium benzoate or BIT (1,2-benzoisothiazolin-3-one).

The said antifoaming agent is a silicone one.

The said antifreezing agent is selected from the group consisting of ethylene glycol, propylene glycol, glycerol, urea or inorganic salts such as sodium chloride.

The dispersing agent, wetting agent, thickener, preservative, antifoaming agent and antifreezing agent used for preparing the suspension are currently commercially available in the market.

The oil suspension can be formulated by the skilled in the art by using the conventional methods with dispersant, wetting agent, emulsifier, solvent, thickener, preservative, antifoaming agent and antifreezing agent.

The said dispersant is selected from the group consisting of polycarboxylates, lignin sulfonates, alkylnaphthalene sulfonates or TERSPERSE 2425 (produced by Huntsman Corporation, alkylnaphthalene sulfonates).

The said wetting agent is selected from the group consisting of alkylphenol polyoxyethylene ether formaldehyde condensate sulfates, alkylphenol polyoxyethylene ether phosphate, phenethyl phenol polyoxyethylene ether phosphates, alkyl sulfate, alkyl sulfonate, naphthalene sulfonate or TERSPERSE 2500 (produced by Huntsman Corporation).

The said emulsifier is selected from the group consisting of nonylphenol polyoxyethylene (EO=10) ether phosphate, triphenylethyl phenol polyoxyethylene ether phosphate (pesticide emulsifier 600# phosphate), pesticide emulsifier 700#, pesticide emulsifier 2201#, Span-60#, the emulsifiers T-60, TX-10, pesticide emulsifier 1601#, pesticide emulsifier 600# or pesticide emulsifier 400#.

The said solvent is selected from the group consisting of xylene, toluene, cyclohexanone or solvent oil (grade: S-150, S-180, S-200).

The said thickener is selected from the group consisting of xanthan gum, magnesium aluminum silicate or bentonite.

The said preservative is selected from the group consisting of benzoic acid, sodium benzoate or BIT (1,2-benzoisothiazolin-3-one).

The said antifoaming agent is a silicone one.

The said antifreezing agent is selected from the group consisting of ethylene glycol, propylene glycol, glycerol, urea or inorganic salts such as sodium chloride.

The dispersing agent, wetting agent, emulsifier, solvent, thickener, preservative, antifoaming agent and antifreezing agent used for preparing the oil suspension are currently commercially available in the market.

The water dispersible granules can be formulated by the skilled in the art by using the conventional methods with such main additives as dispersant, wetting agent, disintegrant, adhesive and filler.

The said dispersing agent is selected from the group consisting of polycarboxylates, lignin sulphonates or alkylnaphthalene sulphonates.

The said wetting agent is selected from the group consisting of polyoxyethylene alcohol, alkyl sulfate, alkyl sulfonate or naphthyl sulfonate.

The said disintegrant is selected from the group consisting of ammonium sulfate, urea, sucrose, glucose, citric acid, butanedioic acid or sodium bicarbonate.

The said adhesive is selected from the group consisting of diatomaceous earth, maize starch, PVA, cellulose carboxymethyl (ethyl) celluloses and microcrystalline celluloses.

The said filler is selected from the group consisting of diatomaceous earth, kaolin, silica hydrated, calcium carbonate light, sepiolite, talc, attapulgite or clay.

The dispersant, wetting agent, disintegrant, adhesive and filler used for preparing water dispersible granules are currently commercially available in the market.

The aqueous emulsion can be formulated by the skilled in the art by using the conventional methods with such main additives as emulsifier, solvent, stabilizing agent, antifreezing agent, thickener and preservative.

The said emulsifier is selected from the group consisting of nonylphenol polyoxyethylene (EO=10) ether phosphate, triphenylethyl phenol polyoxyethylene ether phosphate (pesticide emulsifier 600# phosphate), pesticide emulsifier 700#, pesticide emulsifier 2201#, Span-60#, the emulsifiers T-60, TX-10, pesticide emulsifier 1601#, pesticide emulsifier 600# or pesticide emulsifier 400#.

The said solvent is selected from the group consisting of xylene, toluene, cyclohexanone or solvent oil (grade: S-150, S-180, S-200).

The said stabilizer is selected from the group consisting of triphenyl phosphite or epichlorohydrin.

The said antifreezing agent is selected from the group consisting of ethylene glycol, propylene glycol, glycerol, urea or inorganic salts such as sodium chloride.

The said thickener is selected from the group consisting of xanthan gum, bentonite or magnesium aluminum silicate.

The said preservative is selected from the group consisting of BIT (1,2-benzoisothiazolin-3-one) benzoic acid or sodium benzoate.

The emulsifier, solvent, stabilizing agent, antifreezing agent, thickener and preservative used for preparing aqueous emulsion are currently commercially available in the market.

The microemulsion can be formulated by the skilled in the art by using the conventional methods with such main additives as emulsifier, solubilizer, solvent and stabilizing agent.

The said emulsifier is selected from the group consisting of calcium dodecylbenzenesulfonate (pesticide emulsifier 500#), pesticide emulsifier 700#, pesticide emulsifier 2201#, Span-60#, tween-80, TX-10, pesticide emulsifier 1601#, pesticide emulsifier 600# or pesticide emulsifier 400#.

The said solubilizer is selected from the group consisting of methanol, isopropanol, n-butanol or ethanol.

The said solvent is selected from the group consisting of cyclohexanone, N-methylpyrrolidone, xylene, toluene or solvent oil (grade: S-150, S-180, S-200).

The said stabilizer is selected from the group consisting of triphenyl phosphite or epichlorohydrin.

The emulsifier, solubilizer, solvent and stabilizing agent used for preparing microemulsion are currently commercially available in the market.

The emulsifiable concentrate can be formulated by the skilled in the art by using the conventional methods with such main additives as emulsifier, solubilizer, solvent and stabilizing agent.

The said emulsifier is selected from the group consisting of calcium dodecylbenzenesulfonate (pesticide emulsifier 500#), pesticide emulsifier 700#, pesticide emulsifier 2201#, Span-60#, tween-80, TX-10, pesticide emulsifier 1601#, pesticide emulsifier 600# or pesticide emulsifier 400#.

The said solubilizer is selected from the group consisting of methanol, isopropanol, n-butanol or ethanol.

The said solvent is selected from the group consisting of cyclohexanone, N-methylpyrrolidone, xylene, toluene or solvent oil (grade: S-150, S-180, S-200).

The emulsifier, solubilizer, solvent and stabilizing agent used for preparing emulsifiable concentrate are currently commercially available in the market.

The present invention also relates to use of the said compound of the general formula (I) or the composition containing the said compound of the general formula (I) in the prevention and control of the pests in the field of agriculture, forestry and livestock husbandry, such as bollworm, diamondback moth and borers.

When the said compound is used as insecticide, it can be used alone or formulated with other insecticidal active compounds.

The formulation preparation related to the present invention, can adopt the common way of the pesticide in the art as reference. For example, when the spray method is used, the concentration of the formulation of the present invention is 1-500 ppm.

[Beneficial Effects]

The novel Anthranilonitrile compound disclosed in the present invention has a new structure, no cross-resistance to common pesticides and an excellent control effect to the resistant pests. For preventing and controlling of the pests in the field of agriculture, forestry and animal husbandry, it has 98% of mortality in 3 days to diamondback moth and pink borer. In short, the compound of the present invention has such advantages as high efficiency, low toxicity, safe and environmental protection, etc.

[EMBODIMENTS]

The present invention will be better understood by the following examples.

EXAMPLE 1

Synthesis of compound I-1

Compound I-1 is the compound of the general formula (I) in which $R_1$=CH$_3$, $R_2$=Br, $R_3$=Cl and $R_4$=H.

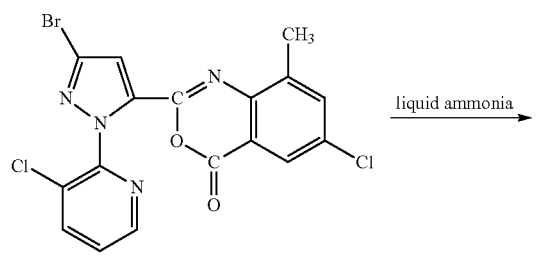

A-1

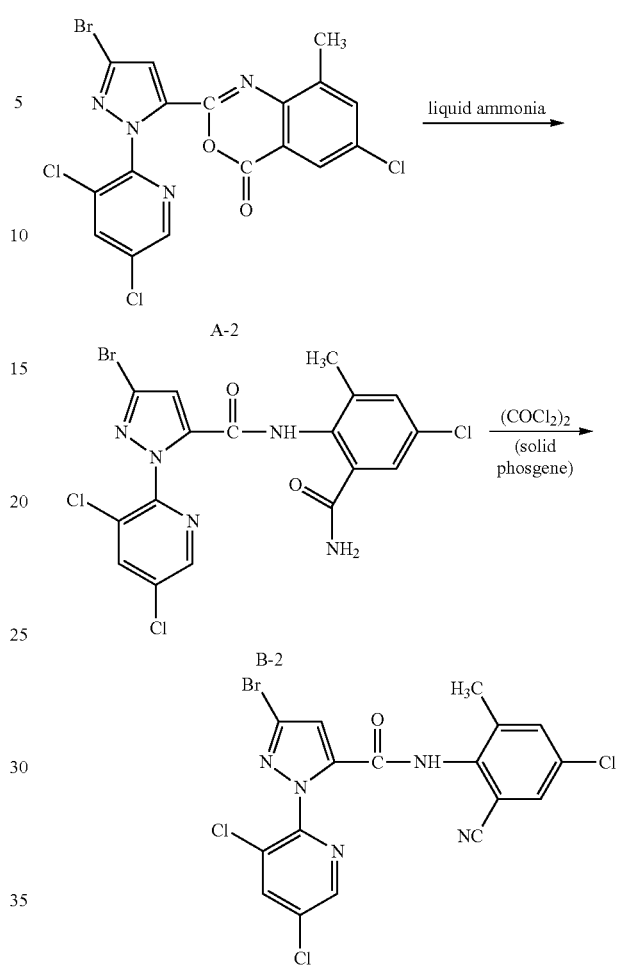

13.5 g of compound A-1 (the compound of the general formula (A) in which $R_1$=$CH_3$, $R_2$=Br, $R_3$=Cl and $R_4$=H) were dissolved in 80 ml of N,N-dimethylformamide. The temperature of the solution was controlled at 10-20° C., then 5 g of aqueous ammonia (ammonia content of 27 wt %) were added drop wise in the solution within 30 min, and kept stirring and reacting for 30 min when drop-wise addition completed. The reaction solution was poured into 120 ml of water, filtered, and the resultant precipitate was dried to give 13.0 g of compound B-1 as white solid.

13.0 g of compound B-1 were dissolved in 100 ml of acetonitrile. 15 g of phosphorus oxychloride were added with stifling, followed by heating at reflux and reacting for 5 h; and 50 ml of acetonitrile were distilled off, and then cooled to the temperature below 10° C. 30 ml of water were added drop wise to the solution, solid precipitate appeared, and the temperature of the solution was controlled at 10-20° C. The solution was neutralized with 15 wt % NaOH solution to reach pH=4-6. The precipitate occurred was then pumped and filtered, the filter cake was washed with appropriate amount of water and then dried. 10.5 g of the title compound I-1 as white solid thus obtained were determined by the nuclear magnetic resonance spectroscopy described in the present specification, the results are as follows:

$^1$H NMR(DMSO-d6)(ppm): 1.96(3H, s), 7.46(1H, s), 7.72 (1H, m), 7.93(1H, d), 8.01(1H, d), 8.31(1H, dd), 8.55 (1H, dd).

EXAMPLE 2

Synthesis of Compound I-2

Compound I-2 is the compound of the general formula (I) in which $R_1$=$CH_3$, $R_2$=Br, $R_3$=Cl and $R_4$=Cl.

10.0 g of compound A-2 (the compound of the general formula (A) in which $R_1$=$CH_3$, $R_2$=Br, $R_3$=Cl and $R_4$=Cl) were weighed and dissolved in 70 ml of N,N-dimethylformamide. The temperature of the solution was controlled at 5-15° C., then 4 g of aqueous ammonia (ammonia content of 27 wt %) were added drop wise in the solution within 30 min, and kept stifling for 30 min when drop-wise addition completed. The reaction solution was poured into 80 ml of water, filtered, and the resultant precipitate was dried to obtain 9.7 g of compound B-2 as white solid.

9.7 g of compound B-1 were weighed and added into 70 ml of toluene, heated to the temperature 110° C. The solution composed of 4 g of solid phosgene and 30 ml of toluene was added drop wise in the solution within 50 min, and kept reacting for 30 min when drop-wise addition completed. Then 80 ml of toluene was distilled off under reduced pressure. The temperature was lowered to room temperature. The precipitate occurred was then pumped, filtered, and the resultant precipitate was dried to obtain 9.2 g of the title compound I-2 as white solid. The compound was determined by the nuclear magnetic resonance spectroscopy described in the present specification, the results are as follows:

$^1$H NMR(DMSO-d6)(ppm): 2.21(3H, s), 7.45(1H, s), 7.79 (1H, d), 7.93(1H, d), 8.54(1H, d), 8.62(1H, d), 10.91(1H, s).

EXAMPLE 3

Synthesis of compound I-3

Compound I-3 is the compound of the general formula (I) in which $R_1$=$CH_3$, $R_2$=Br, $R_3$=F and $R_4$=Cl.

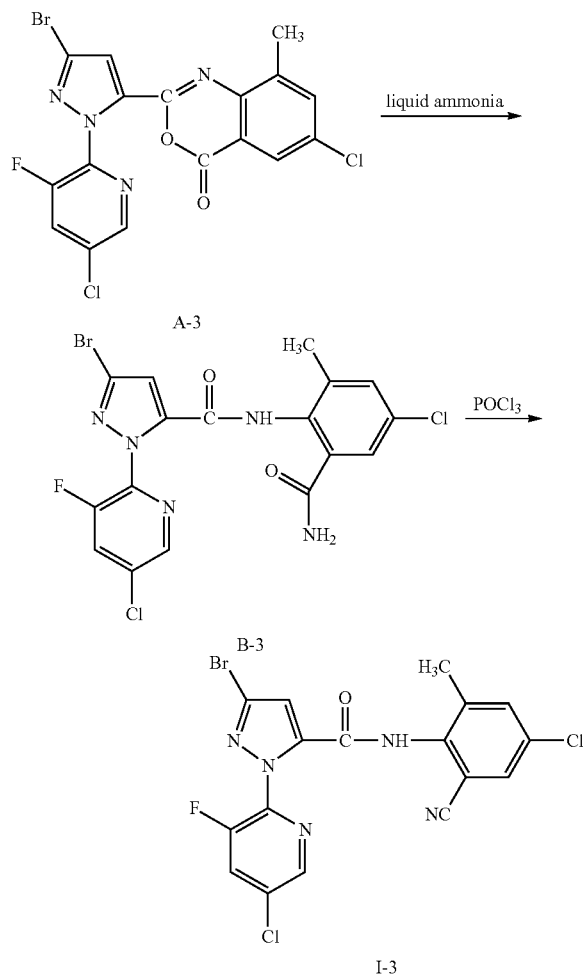

19 g of compound A-3 (the compound of the general formula (A) in which $R_1$=$CH_3$, $R_2$=Br, $R_3$=F and $R_4$=Cl) were weighed and added in 100 ml of N,N-dimethylformamide, then dissolved with stifling. The temperature of the solution was controlled at 0-10° C., then 10 g of N,N-dimethylformamide in aqueous ammonia (ammonia content of 10 wt %) were added drop wise in the solution within 30 min, and kept stirring and reacting for 30 min when drop-wise addition completed. The reaction solution was poured into 150 ml of water. The precipitate occurred was distilled off and the resultant precipitate was dried to obtain 18.3 g of compound B-3, a white solid.

10.0 g of compound B-3 were weighed and added into the 100 ml of ethyl acetate. 10 g of $POCl_3$ were added drop wise into the solution within 30 min under the condition of heating to reflux. By using the rotary evaporation, the solvent was distilled off. 100 ml of water were added, then pumped and filtered. The filter cake was washed with appropriate amount of water and then dried. 8.9 g of the title compound I-3 as white solid thus obtained were determined by the nuclear magnetic resonance spectroscopy described in the present specification, the results are as follows:

$^1$H NMR(DMSO-d6)(ppm): 2.13(3H, s), 7.49(1H, s), 7.68 (1H, d), 8.05(1H, d), 8.26(1H, d), 8.51(1H, d).

EXAMPLE 4

Synthesis of compound I-4

Compound I-4 is the compound of the general formula (I) in which $R_1$=Cl, $R_2$=Br, $R_3$=Cl and $R_4$=H.

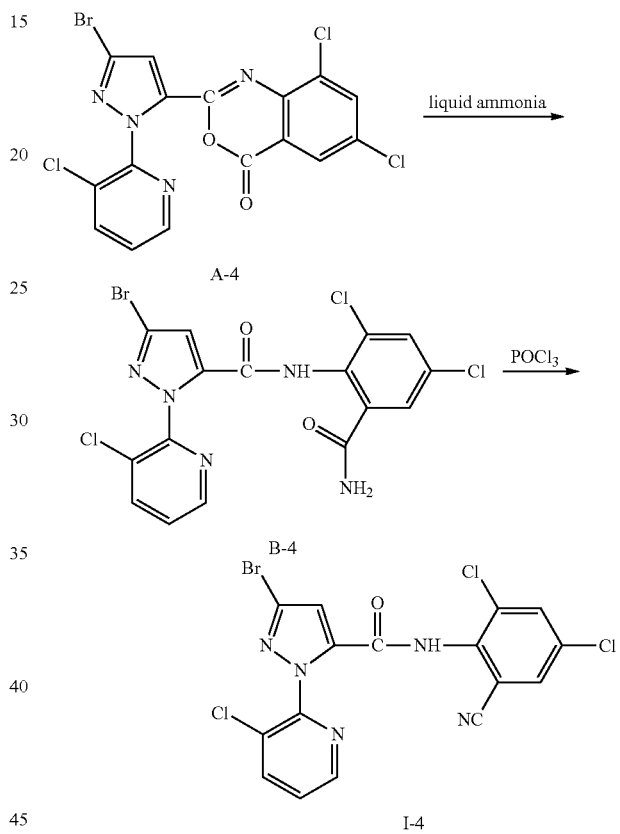

4.7 g of compound A-4 (the compound of the general formula (A) in which $R_1$=Cl, $R_2$=Br, $R_3$=Cl and $R_4$=H) were weighed and dissolved in 40 ml of N,N-dimethylformamide. The temperature of the solution was controlled at 10-20° C., then 2.0 g of aqueous ammonia (ammonia content of 27 wt %) were added drop wise in the solution, and kept stifling for 30 min when drop-wise addition completed. The reaction solution was poured into 50 ml of water. The precipitate occurred was pumped and filtered. Then the resultant precipitate was dried to obtain 4.6 g of compound B-4.

4.6 g of compound B-4 were dissolved in 35 ml of acetonitrile, and then 3.5 g of $POCl_3$ were added. Then solution was heated to reflux for 3 h. By using the rotary evaporation, the solvent was distilled off. 100 ml of water were added, stirred to precipitate solid, then pumped and filtered. The filter cake was washed with appropriate amount of water and then dried. 4.1 g of the title compound I-4 as white solid thus obtained were determined by the nuclear magnetic resonance spectroscopy described in the present specification, the results are as follows:

$^1$H NMR(DMSO-d6)(ppm): 7.52(1H, s), 7.67(1H, m), 7.82(1H, d), 8.24(1H, d), 8.28(1H, dd), 8.33(1H, d), 8.54(1H, dd).

EXAMPLE 5

Synthesis of Compound I-5

Compound I-5 is the compound of the general formula (I) in which $R_1$=Cl, $R_2$=Br, $R_3$=Cl and $R_4$=Cl.

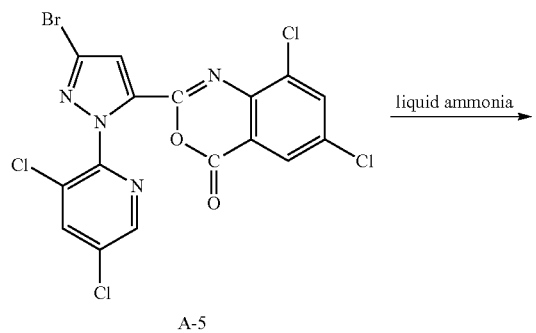

A-5

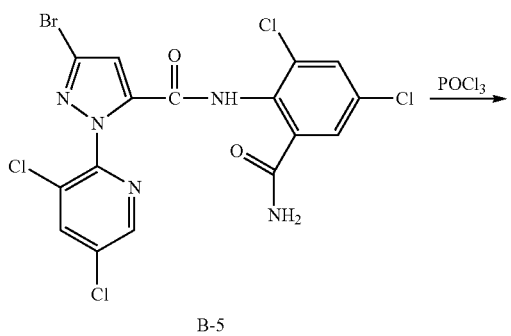

B-5

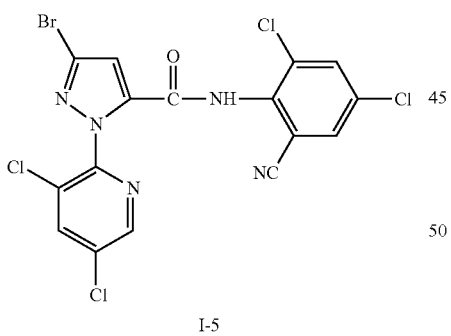

I-5

The example was implemented by the same manner as that of Example 1, only except for reacting the compound A-5 (the compound of the general formula (A) in which $R_1$=Cl, $R_2$=Br, $R_3$=Cl and $R_4$=Cl) with aqueous ammonia to obtain the title compound I-5. The compound I-5 was determined by the nuclear magnetic resonance spectroscopy described in the present specification, the results are as follows:

$^1$H NMR(DMSO-d6)(ppm): 7.33(1H, s), 8.62(1H, d), 8.68 (1H, d), 8.71(1H, d), 8.74(1H, d).

EXAMPLE 6

Synthesis of Compound I-6

Compound I-6 is the compound of the general formula (I) in which $R_1$=Cl, $R_2$=Br, $R_3$=F and $R_4$=Cl.

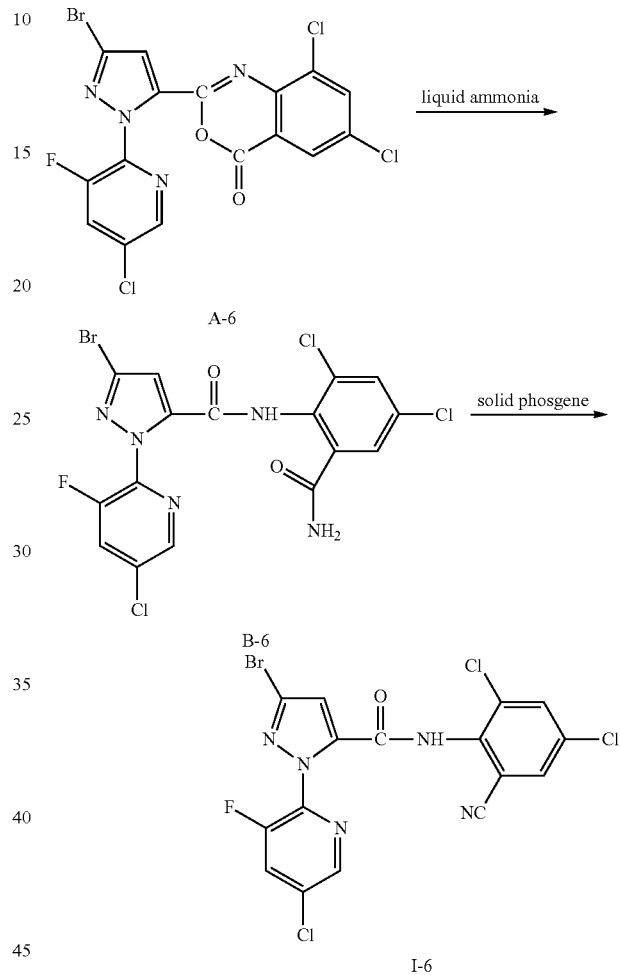

The example was implemented by the same manner as Example 2, only except for using the compound A-6 (the compound of the general formula (A) in which $R_1$=Cl, $R_2$=Br, $R_3$=F and $R_4$=Cl) with aqueous ammonia to obtain the compound B-6, then the compound B-6 with solid phosgene in toluene solution to give the title compound I-6. The compound I-6 was determined by the nuclear magnetic resonance spectroscopy described in the present specification, the results are as follows:

$^1$H NMR(DMSO-d6)(ppm): 7.75(1H, s), 7.84(1H, d), 8.48 (1H, d), 8.50(1H, d), 8.59(1H, d).

EXAMPLE 7

Synthesis of Compound I-7

Compound I-7 is the compound of the general formula (I) in which $R_1$=CH$_3$, $R_2$=Br, $R_3$=Cl and $R_4$=CF$_3$.

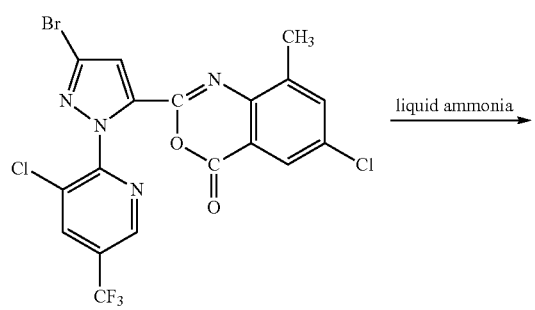

A-7

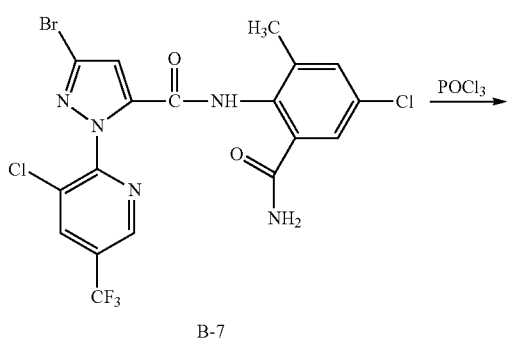

B-7

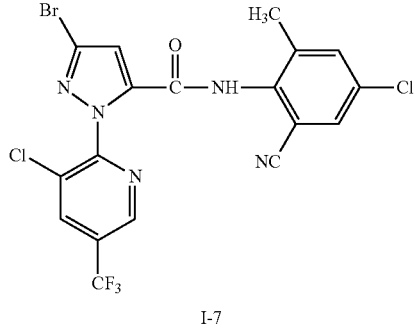

I-7

The example was implemented by the same manner as Example 4, only except for using compound A-7 (the compound of the general formula (A) in which $R_1$=CH$_3$, $R_2$=Br, $R_3$=Cl and $R_4$=CF$_3$) with aqueous ammonia to obtain the compound B-7, then the compound B-7 with POCl$_3$ to give the title compound I-7. The compound I-7 was determined by the nuclear magnetic resonance spectroscopy described in the present specification, the results are as follows:

$^1$H NMR(DMSO-d6)(ppm): 2.13(3H, s), 7.46(1H, s), 7.63 (1H, d), 8.01(1H, d), 8.19(1H, d), 8.42(1H, d)

The basic data of the compounds prepared according to Examples 1-7 is summarized in the following table:

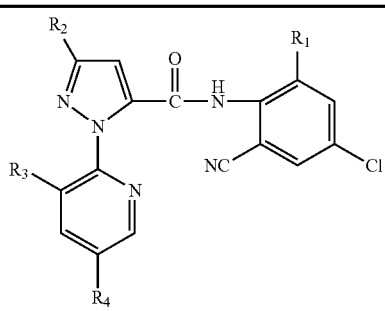

| Compound I | $R_1$ | $R_2$ | $R_3$ | $R_4$ | Physical Properties | melting point/° C. |
|---|---|---|---|---|---|---|
| I-1 | CH$_3$ | Br | Cl | H | white solid | 266-269 |
| I-2 | CH$_3$ | Br | Cl | Cl | white solid | 254-256 |
| I-3 | CH$_3$ | Br | F | Cl | white solid | 271-273 |
| I-4 | Cl | Br | Cl | H | white solid | 243-246 |
| I-5 | Cl | Br | Cl | Cl | white solid | 258-260 |
| I-6 | Cl | Br | F | Cl | white solid | 263-265 |
| I-7 | CH$_3$ | Br | Cl | CF$_3$ | white solid | 251-254 |

The formulation examples are described as follows, in which the compound of the present invention is as an active ingredient, and the said formulation can be used as insecticides in the field of agriculture, forestry, animal husbandry.

FORMULATION EXAMPLE 1

Aqueous Emulsion 10 parts by weight of compound I-1 prepared in Example 1 of the present invention, 10 parts by weight of cyclohexanone, 10 parts by weight of xylene, 8 parts by weight of pesticide emulsifier 600# phosphate, 10 parts by weight of 1 wt % xanthan gum, 5 parts by weight of ethylene glycol and 47 parts by weight of water were processed according to the conventional processing technique of aqueous emulsion to obtain an aqueous emulsion containing 10% Compound I-1 as the active ingredient.

FORMULATION EXAMPLE 2

Suspension 20 parts by weight of compound I-3 prepared in Example 3 of the present invention, 3 parts by weight of the dispersing agent NNO (sodium methylenedinaphthalene disulphonate), 2 parts by weight of pesticide emulsifier 1601#, 2 parts by weight of magnesium aluminum silicate as suspending agent, 4 parts by weight of ethylene glycol as antifreezing agent, 1 parts by weight of organosilicon as defoamer and 68 parts by weight of water were processed according to the conventional processing technique of suspension to obtain an suspension containing 20% Compound I-3 as the active ingredient.

FORMULATION EXAMPLE 3

Oil Suspension 15 parts by weight of compounds I-4 prepared in Example 4 of the present invention, 6 parts by weight of Span-80, 5 parts by weight of Tween T-80, 3 parts by weight of fatty alcohol polyoxyethylene ether, 2 parts by weight of nonylphenol poly(ethylene oxide) ether, 1 part by weight of silica hydrated, 1 parts by weight of organic bentonite, 1 part by weight of the methylated vegetable oil, and methyl oleateto which made up the total oil suspension of 100 parts by weight were added in a high shear emulsifying machine and sheared for 10 min, then sanded with sand mill to give an oil suspension containing 15 wt % of Compound I-4 as the active ingredient.

FORMULATION EXAMPLE 4

Water Dispersible Granule 30 weight parts of compound I-5 prepared in Example 5 of the present invention, 4 parts by weight of NNO (alkyl naphthalene sulphonate formaldehyde condensates), 2 parts by weight of Nekal BX (sodium dibutylnaphthalene sulphonate), 3 parts by weight of K-12 (odium dodecyl sulfate), 5 parts by weight of carboxymethyl(ethyl)cellulose, 10 parts by weight of silica hydrated, 15 parts by weight of glucose, and kaolin which made up the total water dispersible granule of 100 parts by weight were uniformly mixed. The mixture was pulverized by the airflow, granulated in a granulator, and then dried and sieved to obtain a granular product of 30 wt % water dispersible granules.

FORMULATION EXAMPLE 5

Microemulsion 10 parts by weight of compound I-1 prepared in Example 1 of the present invention, 15 parts by weight of cyclohexanone, 5 parts by weight of N-methylpyrrolidone, 6 parts by weight of pesticide emulsifier 600# phosphate, 7 parts by weight of pesticide emulsifier 500#, 5 parts by weight of pesticide emulsifier 1601#, 5 parts by weight of n-butanol and water which made up the total microemulsion of 100 parts by weight, were used. According to the formulation, the original drug, emulsifiers and solvents were added in the ingredients kettle, completely dissolved and mixed well. Then deionized water was added to make up the total microemulsion of 100 parts by weight. Then kept mixing until the solution became transparency to obtain a micromulsion containing 10 wt % of Compound I-1 as the active ingredient.

FORMULATION EXAMPLE 6

Emulsifiable Concentrate

The following materials were processed according to common processing technique to obtain an emulsifiable concentrate containing 10 wt % of Compound I-6 as the active ingredient: 10 parts by weight of compound I-6 prepared in Example 6 of the present invention, 15 parts by weight of cyclohexanone, 8 parts by weight of pesticide emulsifier 500#, 4 parts by weight of pesticide emulsifier 1601#, and solvent oil 150 which made up the total emulsifiable concentrate of 100 parts by weight.

The following are pesticide tests cases using the compound I of the present invention as active ingredients.

TEST EXAMPLE 1

Insecticidal Effect on Diamondback Moth

The compound to be tested dissolved in acetone and 1‰ Tween-80 solution, and was formulated to 50 ml of the test solution with desired concentration. The cabbage leaves having been cleaned and dried were made into leaf disc with diameter of 1 cm with hole puncher. The leaf disc were immersed in the drug liquid for 10 seconds and then removed, dried naturally, loaded in the culture dish. 10 3-year-old diamondback moth larvae were introduced per dish and repeated for three times. After the treatment, the dishes were placed into a room with temperature of 20° C., relative humidity of 60-70% and without illumination to take an indoor culture. The survival of insects was surveyed and the mortality was calculated. The test results are shown in the following Table 1.

TEST EXAMPLE 2

Insecticidal Effect on Pink Stem Borer

The test example was carried out in accordance with the method of Test Example 1, except for using the test Pink Borer. The test results are shown in the following Table 1.

TABLE 1

Results of Insecticidal Effect Test of the Compound 1 of the Present Invention

| | Insecticidal Effect (%) | |
|---|---|---|
| Compound | Diamondback moth (1 mg/L) | pink stem borer (2 mg/L) |
| I-1 | 50 | 40 |
| I-2 | 80 | 50 |
| I-3 | 100 | 85 |
| I-4 | 100 | 98 |
| I-5 | 100 | 70 |
| I-6 | 100 | 90 |
| I-7 | 90 | 80 |

The inventive compound of I-3, I-4, I-5, I-6, each has 100% of mortality to diamondback moth in 3 days, with the concentration of 1 mg/L; In particular, the compound I-4 has 98% of mortality to pink stem borer in 3 days, with the concentration of 2 mg/L.

What is claimed is:
1. An anthranilonitrile compound has a chemical general formula (I) as shown as:

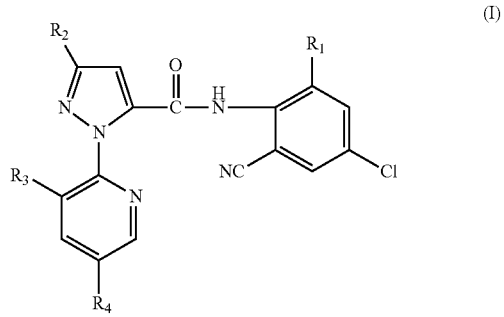

wherein,
R$_1$ is Cl, Br or methyl;
R$_2$ is Br, Cl, CF$_3$, propynyloxy or haloalkoxy; the halogen in said haloalkoxy is one or more halogen(s) selected from fluorine, chlorine or bromine;
R$_3$ is Cl or F;
R$_4$ is H, Cl or CF$_3$.
2. The anthranilonitrile compound according to claim 1, wherein said formula (I):
R$_1$ is Cl, Br or methyl;

$R_2$ is Cl, Br or $CF_3$;
$R_3$ is Cl or F;
$R_4$ is H or Cl.

3. The anthranilonitrile compound according to claim 1, wherein said formula (I):
$R_1$ is Cl or methyl;
$R_2$ is Cl or Br;
$R_3$ is Cl or F;
$R_4$ is H or Cl.

4. A process for preparing the anthranilonitrile compound of claim 1, comprising the following steps:
 i) a compound A having a chemical formula A is reacted with ammonia or liquid ammonia in a polar aprotic solvent at temperature between −10 and 40° C. which results in compound B having a chemical formula B; and then
 ii) said compound B is reacted with dehydrating agent C in an aprotic solvent and at temperature between 20 and 120° C. to obtain the compound of claim 1:

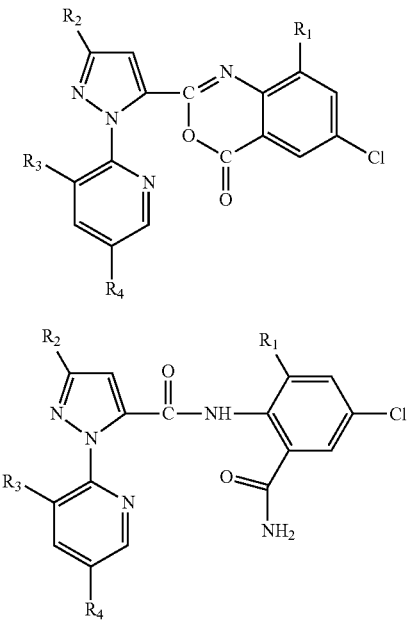

in which,
$R_1$, $R_2$, $R_3$ and $R_4$ are as defined in claim 1;
said dehydrating agent C is $POCl_3$, $P_2O_5$, phosgene or solid phosgene;
said polar aprotic solvent is amides or nitrile solvent; said amides solvent is selected from the group consisting of N,N-dimethylformamide, N,N-dimethylacetamide and N-methylpyrrolidone; said nitrile solvent is acetonitrile or propionitrile;
said aprotic solvent is selected from the group consisting of nitrile, ester and benzol solvents; said nitrile solvent is acetonitrile or propionitrile; said ester solvent is ethyl acetate; said benzol solvent is toluene.

5. The process according to claim 4, wherein said compound A is reacted with ammonia or liquid ammonia under the temperature of −5-10° C. to obtain the said compound B.

6. The process according to claim 4, wherein the compound B is reacted with dehydrating agent C under the temperature of 70-90° C. obtain the compound of the said general formula (I).

7. An insecticidal composition, wherein the insecticidal composition is composed of 0.1-80.0% by weight of the compound of the said general formula (I) according to any of claims 1-4 as active ingredient and 20.0-99.9% by weight of the pesticidally acceptable carriers and auxiliaries.

8. The composition according to claim 7, characterized in that the insecticidal composition is composed of 5.0-30.0% by weight of the compound of the said general formula (I) according to any of claims 1-4 as active ingredient and 70.0-95.0% by weight of pesticidally acceptable carriers and auxiliaries.

9. The composition according to claim 7, wherein the formulation of the composition is suspension, oil suspension, water dispersible granules, aqueous emulsion, microemulsion or emulsifiable concentrate.

* * * * *